United States Patent [19]

Smith et al.

[11] 4,140,004
[45] Feb. 20, 1979

[54] APPARATUS FOR DETERMINING THE EXPLOSION LIMITS OF A FLAMMABLE GAS

[75] Inventors: Harvey N. Smith, Putnam Valley, N.Y.; Michael A. Woolf, Northampton, Mass.

[73] Assignee: Stauffer Chemical Company, Westport, Conn.

[21] Appl. No.: 849,917

[22] Filed: Nov. 9, 1977

[51] Int. Cl.² .................................................. G01N 25/54
[52] U.S. Cl. ........................................... 73/26; 73/35; 73/36
[58] Field of Search ............................... 73/26, 35, 36; 60/39.82 R, 39.82 E, 632; 431/99

[56] References Cited

U.S. PATENT DOCUMENTS

| 1,627,204 | 5/1927 | Ruben ........................................ 73/26 |
| 3,768,313 | 10/1973 | Johansson et al. ....................... 73/35 |

FOREIGN PATENT DOCUMENTS 158432  1/1964  U.S.S.R. ........................................ 73/35

OTHER PUBLICATIONS

"Exploded Wire Studied for Use in Space Thrust" from Research and Development, Oct. 1960.

Primary Examiner—James J. Gill
Attorney, Agent, or Firm—Michael E. Zall

[57] ABSTRACT

An apparatus for determining the explosion limits of flammable gases having a combustion chamber, a conduit leading to the combustion chamber for conveying the sample stream of gas, a temperature control for maintaining the gas in the combustion chamber at a predetermined temperature and an ignition system for igniting the gas. The ignition system includes an exploding wire powered by a low internal resistance battery, thus enabling the testing of corrosive, flammable gases.

17 Claims, 7 Drawing Figures

APPARATUS FOR DETERMINING THE EXPLOSION LIMITS OF A FLAMMABLE GAS

BACKGROUND OF THE INVENTION

This invention relates to an apparatus for determining the explosion limits of a flammable gas. More particularly, the invention relates to an apparatus which safely withdraws and ignites wet, corrosive, flammable gases from gas streams and determines the lower or upper explosion limit of the gases.

Various devices for determining the explosive characteristics of gases have been previously described. For example, U.S. Pat. No. 263,939 describes an automatic system for continuously testing air, containing methane, in a mine. In this system, air is pulled from the mine by bellows into a chamber where it is ignited by a spark from an induction-coil or an incandescent platinum wire. The resulting pressure increase is sensed by a manometer. A similiar system is described in U.S. Pat. No. 977,947 with the exception that the explosion is indicated by an audible and visible signal. In U.S. Pat. No. 3,026,711, a certain quantity of a flammable gas is compressed and the heat of combustion measured by such means as a thermocouple. If desired, a measuring tube made of transparent material can be affixed to the compression chamber. The apparatus described in U.S. Pat. No. 3,768,313 is used to determine the least amount of energy to ignite a gas by the spark gap ignition method.

Other devices to measure characteristics of flammable gases have also been described in the prior art. Thus, U.S. Pat. No. 3,027,751 describes means for observing the velocity of a blast wave by measuring the change in resistance of a wire at the locus of a moving flame front, while the detector described in U.S. Pat. No. 3,315,081 employs photocells to measure the burn time of a sample ignited by a spark. In U.S. Pat. No. 3,434,336, an explosion barrier is described in which hot wires, sparks from impact, spontaneous combustion, static, etc. are used to ignite a gas in a two-chamber explosion test apparatus. The device described in U.S. Pat. No. 3,978,877 employs spark plug ignition from a conventional capacitive discharge ignition unit to detect flammable gas mixtures.

While suitable for specific applications, none of the prior art devices are adequate for detecting the explosion limits of corrosive gases, and particularly wet, corrosive gases. Accordingly, there is a need for a device which will allow for the sampling and testing of corrosive gases from process streams, waste streams, etc., in a reproducible manner without damaging the test apparatus.

SUMMARY OF THE INVENTION

It is an object of this invention to provide an apparatus for determining the explosion limits of a flammable gas.

It is a further object of this invention to provide an apparatus which allows for the determination of the explosion limits of wet, corrosive, flammable gases, such as those obtained from process streams, waste streams, etc.

It is another object of this invention to provide an apparatus for determining the explosion limits of flammable gases which has safety features to provide for isolation of the flammable gas within the combustion area.

It is another object of this invention to provide means for supplying a reproducible amount of energy to an ignition system for flammable gases so that meaningful comparisons of data may be made.

It is still another object of this invention to provide a device for testing the explosion limits of a flammable gas at the same temperature as the temperature of the gas stream from which the sample is taken.

Another object of this invention is to provide visual observation means for the flame produced in the apparatus of this invention.

It is yet another object of this invention to provide means for determining the velocity of the flame produced in the apparatus of this invention.

Another object of this invention is to provide means for testing the pressure in the flame produced in the apparatus of this invention.

It is another object of the invention to provide means for testing the temperature of the flame produced in the apparatus of this invention.

According to this invention, an apparatus is provided which includes a combustion chamber having an inlet and an outlet, conduit means communicating with the inlet of the combustion chamber for conveying a sample stream of gas to the combustion chamber, and ignition means connected with the combustion chamber and comprising an exploding wire powered by a low internal resistance battery.

DETAILED DESCRIPTION OF THE INVENTION

Figure 1:
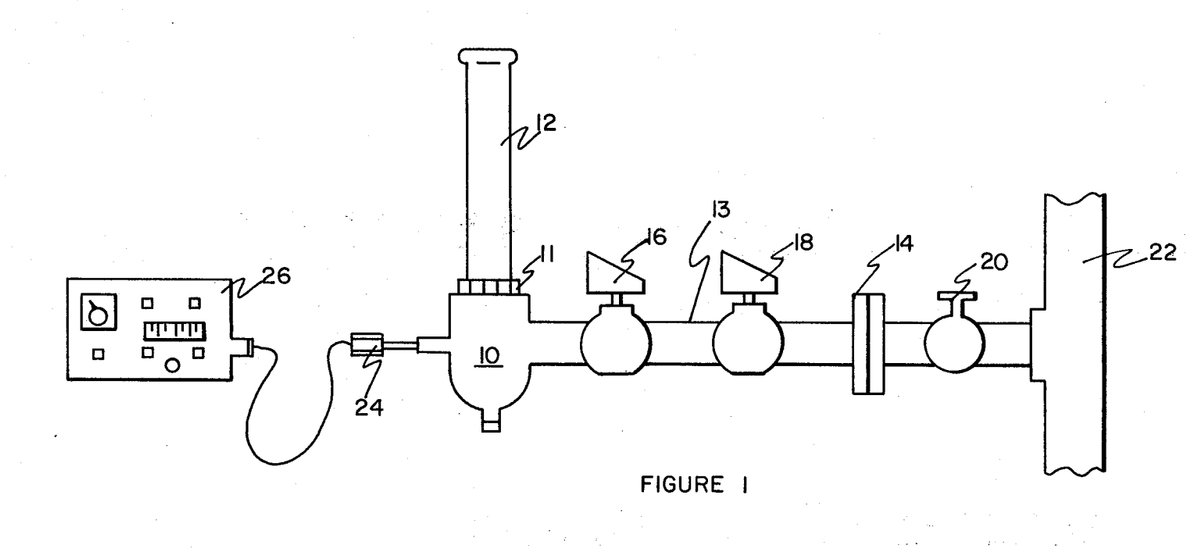
FIG. 1 is a diagrammatic view of an apparatus of the invention connected to a gas-stream and ready for operation.

Referring to FIG. 1, there is shown an apparatus having a combustion chamber 10 connected by adjustable collar 11 to flame propagation chamber 12. Conduit means 13 lead into combustion chamber 10 and terminate at the other end in flange 14. Safety interlocked ball valves 16 and 18 insure isolation of the gas sample from the gas stream. The apparatus is connected by flange 14 to the system to be sampled, shown as full port ball valve 20 leading from gas stream 22. The apparatus also includes ignition probe 24 and control module 26, which will be described in detail below. Preferably, the conduit means and combustion chamber are made of stainless steel, although any metal compatible with the gas stream can be used. The flame propagation chamber can be made of stainless steel, glass or any other suitable material. It should also be noted that configurations other than cylindrical can be used for the flame propagation chamber. Where safety valves are desired, either dual valves or a single valve can be used. Thus, a single valve interlocked to the ignition source to prevent flashback can be employed.

In operation, the gas stream to be tested enters the apparatus of this invention through flange 14 and flows past dual safety interlocked ball valves 16 and 18 to combustion chamber 10 and then up vertical flame propagation chamber 12, which is unrestricted at the top, allowing the gas to vent. Preferably, a conventional flame arrestor (not shown) is provided at the top of flame propagation chamber 12. When the apparatus has been flushed and filled with entering gas, valves 16 and 18 are closed to prevent flashback into the process stream. After a suitable time for turbulence to damp down, the gas is ignited by means of ignition probe 24. The properties of the combustion are observed visually in flame propagation chamber 12 where this chamber is made of a transparent material, and/or sensed by appropriate indicating means on control module 26.

Figure 2:
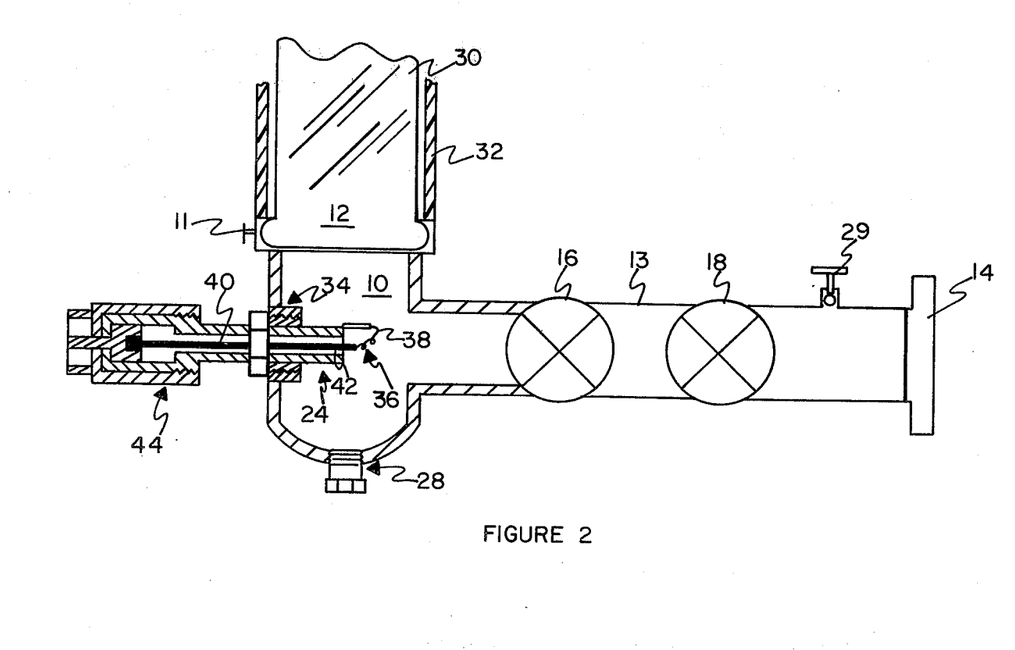
FIG. 2 is a front elevational view, partly in section of one embodiment of the apparatus of the invention.

Referring to FIG. 2, combustion chamber 10 is provided with drain and plug 28, for removing any condensable materials remaining after testing. The conduit means also has sampling port 29 for removing a sample of the gas, should other types of analysis be desired. In this preferred embodiment, the flame propagation chamber 12 includes transparent tubing 30 surrounded by protective shell 32, which may be made of high-impact plastic. An opening in this protective shell provides for visual observation of the flame through transparent tubing 30. Ignition probe 24 includes a threaded connection 34 to combustion chamber 10 and probe terminal 36 including exploding wire 38. The exploding wire can be made of platinum, silver, nickel-chromium, or any conductive material compatible with the gas stream. It may be replaced in between tests, or means for continuously providing a new supply of wire after each test can be provided. Probe body 40 is surrounded by ceramic insulator 42 and terminates in coaxial connector 44, which connects with a battery (not shown).

Figure 3:
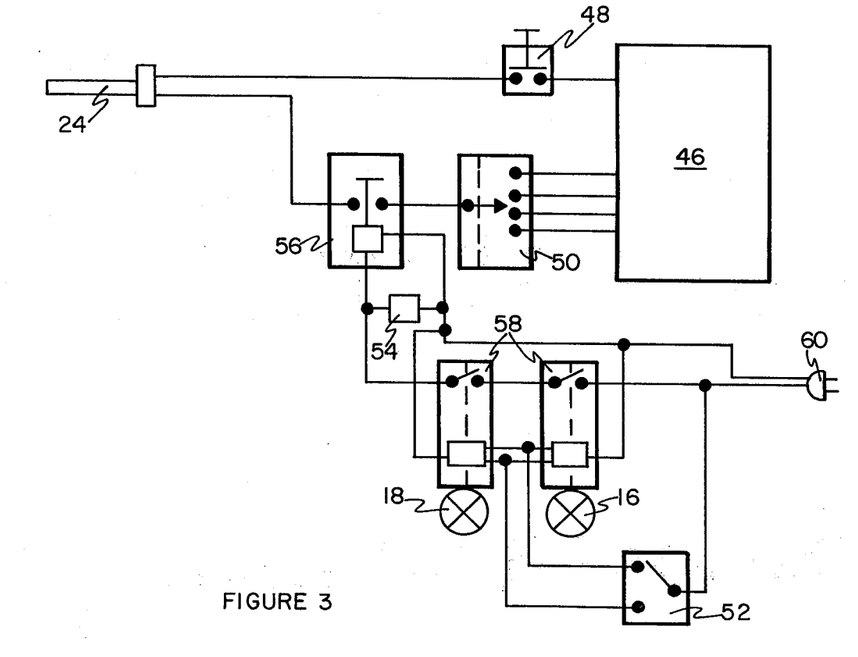
FIG. 3 is a block circuit diagram showing both ignition systems and valve systems of the apparatus of this invention.

In FIG. 3, the low internal resistance battery used to power the ignition source is designated at 46. By the term "low internal resistance" in the claims and specification herein is meant a resistance of less than $10 \times 10^{-3}$ ohms per cell. Exemplary batteries include sealed lead-acid cells, nickel-cadmium cells, etc. The batteries are selected to provide a total voltage of from about 50 to about 150 volts, and preferably from about 95 to about 120 volts. For example, a battery pack consisting of 48 rechargeable sealed lead-acid cells, each cell having an internal resistance of less than $10 \times 10^{-3}$ ohms, or 80 rechargeable nickel-cadmium cells of 2.2 Amphour capacity, can be suitably employed. The use of battery power provides a safe apparatus, eliminating the possibilities of hazards such as arcing, sparking and the like which are associated with the use of line current. Energy-select switch 50 is used to select the amount of power required for ignition. The power selected is applied to ignition probe 24 by closing manual ignite switch 48. "Open-close" valve switch 52 controls safety interlocked ball valves 16 and 18. The "ready" indicator 54 indicates that both valves are closed, rendering the apparatus suitable for test purposes. Interlock actuator 56 is a switch which closes to complete the circuit upon closing of valves 16 and 18, enabling probe 24 to be fired. The circuitry for the safety interlocked ball valves 14 and 16 is contained within explosion-proof housings 58. Plug 60 is provided for connection to an AC power source for operating the valve motors safety interlocks and heating mantles were necessary.

Figure 4:
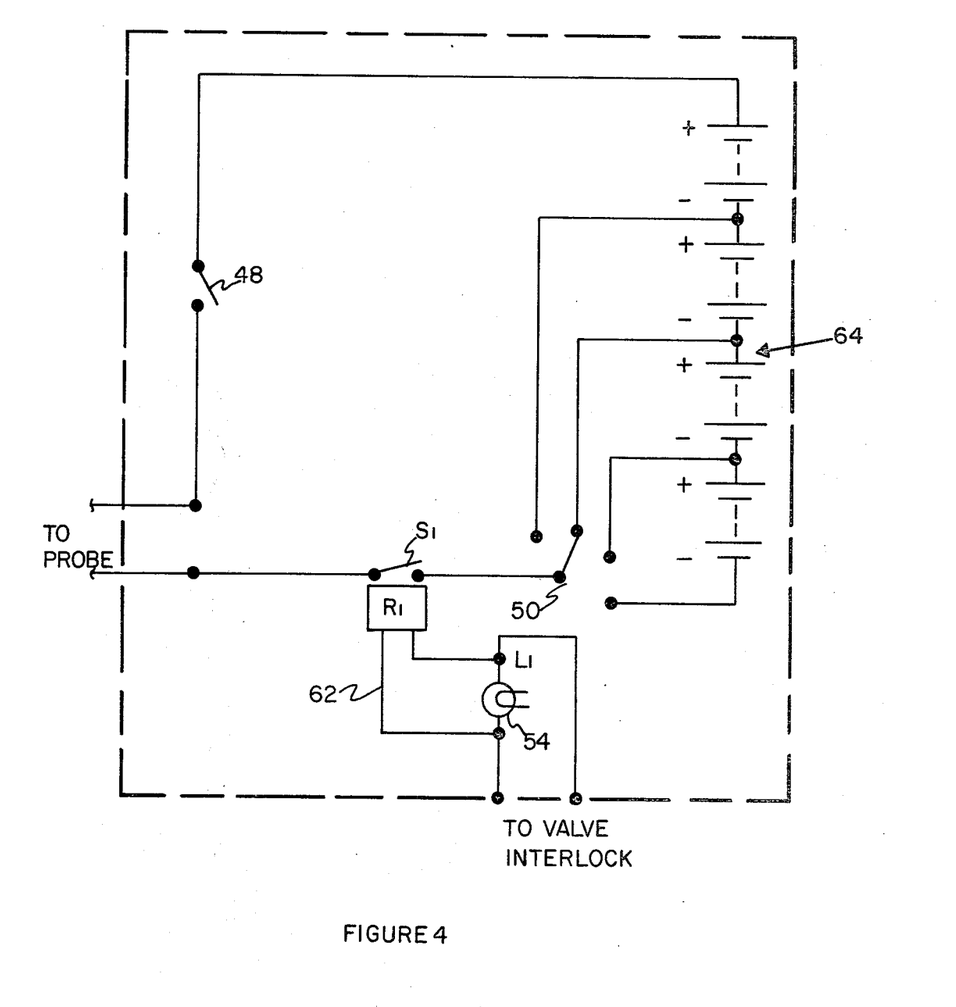
FIG. 4 is a schematic diagram of an ignition system of the apparatus of this invention.

In FIG. 4, an electrical signal from line 62 enters the coil of relay $R_1$ closing contact $S_1/R_1$. Power for exploding the wire probe is obtained from battery pack 64, shown as consisting of cells in series with provisions for tapping off at four different intermediate voltages. Switch 50 selects the required voltage. The battery pack consists of 48 sealed lead-acid "D" cells which are preferred in the apparatus of this invention. The exploding wire is fired by closing switch 48 and applying the selected voltage to the exploding wire.

Figure 5:
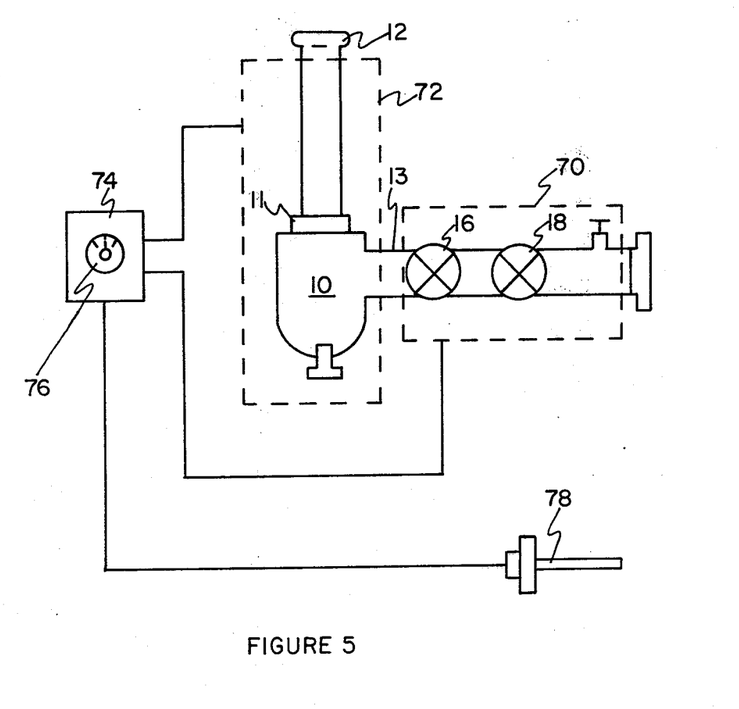
FIG. 5 is a front elevational view, partly in section, showing the temperature control features of the apparatus of this invention.

In FIG. 5, heating mantle for conduit means 13 is represented by 70 and heating mantle for combustion chamber 10 and flame propagation chamber 12 is represented by 72. The temperature controller for heating mantles 70 and 72 is contained within control module 74. A manual set point 76 is on the control module for selecting the desired temperature. The process stream temperature sensor 78 allows one to determine the actual temperature of the gas stream. The temperature of heating mantles 70 and 72 can be set in order to maintain the temperature of the gas in the conduit means 13 and combustion chamber 10 at that level. With some gases, the use of heating mantles 70 and 72 is optional. However, with gases composed of mists or having high vapor content, it is preferable to test under conditions identical to those in the process stream, as may be provided for by the use of heating mantles.

Figure 6:
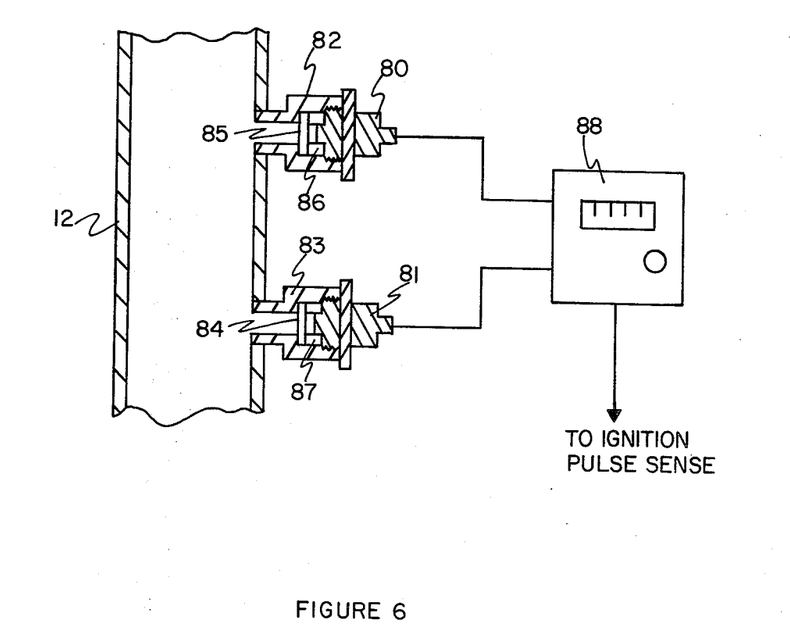
FIG. 6 is a fragmentary elevational view, partly in section, showing a portion of the apparatus of this invention including means for sensing flame velocity.

FIG. 6 depicts a section of a flame propagation chamber 12 equipped for quantitative analysis of flammability. This embodiment measures the velocity of propagation of the flame front along the chamber by automatic electronic timing of the passage of this front by means of phototubes 80 and 81. Phototube ports 82 and 83 contain transparent quartz windows 84 and 85 held in place by spacers 86 and 87. The timing and readout circuit is diagrammatically represented as 88.

Figure 7:
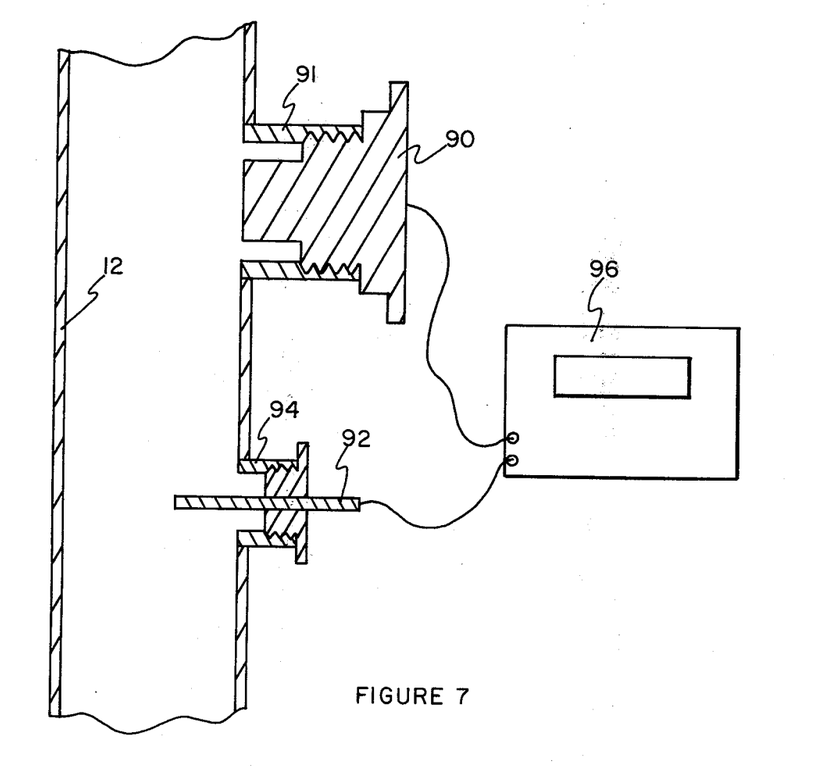
FIG. 7 is a fragmentary elevational view, partly in section, showing a portion of the apparatus of this invention including means for sensing the pressure and temperature of the flames.

In FIG. 7, the pressure of the flame can be measured by strain-gauge type pressure transducer 90 located in pressure transducer port 91 in flame propagation chamber 12. The temperature of the flame can be measured by miniature thermocouple probe 92 positioned in thermocouple port 94. Both pressure transducer 90 and thermocouple probe 92 are electrically connected to a peak detector 96 for read-out of the maximum pressure and temperature.

The apparatus is conveniently portable allowing testing of corrosive, flammable gas streams at various locations. It provides a simple and reliable means for monitoring the combustion properties of flammable gas mixtures.

It should be noted that various combinations of the features depicted above can be employed in the apparatus of this invention. The safety interlocks, the visual observation feature, the measuring device for the velocity of the flame, the means to determine pressure in the flame and temperature in the flame, can be included individually or in combination in an apparatus.

Although the invention has been described in connection with certain preferred embodiments, it is not intended that the invention be limited thereto. It is intended that the invention cover all alternative arrangements, equivalents, and embodiments as may be included in the scope of the following claims.

What is claimed is:

1. An apparatus for determining the explosive characteristics of gases comprising:
   a combustion chamber having an inlet and an outlet
   conduit means communicating with the inlet of said combustion chamber for conveying a sample of gas from a sample source to said combustion chamber;
   ignition means connected with said combustion chamber comprising an exploding wire powered by a low internal resistance battery for igniting the sample of gas; and
   a detection means for detecting the ignition of the sample of gas.

2. The apparatus of claim 1 further including temperature control means for maintaining the gas in said combustion chamber at a predetermined temperature.

3. The apparatus of claim 1 wherein said conduit means includes dual interlocked valves for isolating the gases in said conduit means and combustion chamber from said sample source.

4. The apparatus of claim 3 further including sampling means in said conduit means to allow withdrawal of gas samples.

5. The apparatus of claim 1 wherein said low internal resistance battery provides a total voltage of from about 50 to about 150 volts.

6. The apparatus of claim 5 wherein said low internal resistance battery provides a total voltage of from about 95 to about 120 volts.

7. The apparatus of claim 6 wherein said low internal resistance battery comprises a battery pack of sealed lead-acid cells.

8. The apparatus of claim 6 wherein said low internal resistance battery comprises a battery pack of nickel-cadmium cells.

9. The apparatus of claim 1 wherein said exploding wire is platinum.

10. The apparatus of claim 1 further including a flame propagation chamber connected to said combustion chamber.

11. The apparatus of claim 10 wherein the detection means is a transparent means for viewing said flame and is included in said flame propagation chamber.

12. The apparatus of claim 10 wherein the detection means includes a means for determining flame velocity.

13. The apparatus of claim 12 wherein said means for determining flame velocity comprises at least two phototubes electrically connected to measure the time required for the flame to travel between the phototubes.

14. The apparatus of claim 10 wherein the detection means includes a means for measuring the pressure in the flame.

15. The apparatus of claim 14 wherein said means for measuring the pressure in the flame comprises a pressure transducer.

16. The apparatus of claim 10 wherein the detection means includes a means for sensing the temperature of the flame.

17. The apparatus of claim 16 wherein said means for sensing the temperature of the flame comprises a thermocouple located within said flame propagation chamber.

* * * * *